United States Patent
Kim et al.

(10) Patent No.: US 11,241,517 B2
(45) Date of Patent: Feb. 8, 2022

(54) HYDROGEL COMPOSITION AND BIOINK COMPOSITION INCLUDING THE SAME

(71) Applicant: KOREA INSTITUTE OF SCIENCE AND TECHNOLOGY, Seoul (KR)

(72) Inventors: Sang Heon Kim, Seoul (KR); Joo Young Lee, Seoul (KR); Seung Ja Oh, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 349 days.

(21) Appl. No.: 16/165,515

(22) Filed: Oct. 19, 2018

(65) Prior Publication Data

US 2020/0101194 A1 Apr. 2, 2020

(30) Foreign Application Priority Data

Oct. 2, 2018 (KR) .......................... 10-2018-0117871

(51) Int. Cl.
*A61L 27/24* (2006.01)
*B33Y 70/00* (2020.01)
(Continued)

(52) U.S. Cl.
CPC .............. *A61L 27/24* (2013.01); *A61L 27/20* (2013.01); *A61L 27/222* (2013.01); *A61L 27/26* (2013.01); *A61L 27/38* (2013.01); *A61L 27/52* (2013.01); *B29C 64/40* (2017.08); *B33Y 70/00* (2014.12); *A61L 2430/34* (2013.01); *B29K 2005/00* (2013.01); *B29K 2105/0061* (2013.01); *B29K 2995/0056* (2013.01); *B33Y 10/00* (2014.12)

(58) Field of Classification Search
CPC ........ A61L 27/225; A61L 27/38; A61L 27/26; A61L 27/52; A61L 27/20; A61L 27/24; A61L 27/222; A61L 2430/34; B33Y 80/00; B33Y 70/00; B33Y 10/00; B29C 64/40; B29K 2995/0056; B29K 2105/0061; B29K 2005/00
See application file for complete search history.

(56) References Cited

U.S. PATENT DOCUMENTS

2011/0256089 A1 10/2011 Lim et al.
2012/0089238 A1 4/2012 Kang et al.
2018/0280578 A1 10/2018 Hwang

FOREIGN PATENT DOCUMENTS

EP   3326661 A1 * 5/2018 ............. A61L 27/22
EP   3326661 A1   5/2018
(Continued)

OTHER PUBLICATIONS

Extended European Search Report for European Application No. 19174978.7, dated Dec. 18, 2019.

*Primary Examiner* — Blessing M Fubara
(74) *Attorney, Agent, or Firm* — Birch, Stewart, Kolasch & Birch, LLP

(57) ABSTRACT

Provided are a hydrogel composition with high viscoelasticity and a bioink composition including the hydrogel composition. The hydrogel composition according to an embodiment is composed of natural biocompatible substances and thus is not toxic, but has high viscosity, resulting in high mechanical stability or long persistence. Thus, the hydrogel composition may be usefully utilized as a bioink composition for bioprinting, a support in tissue engineering, or a soft tissue filler.

7 Claims, 7 Drawing Sheets

(51) Int. Cl.
  *B29C 64/40*   (2017.01)
  *A61L 27/20*   (2006.01)
  *A61L 27/22*   (2006.01)
  *A61L 27/26*   (2006.01)
  *A61L 27/38*   (2006.01)
  *A61L 27/52*   (2006.01)
  *B33Y 10/00*   (2015.01)
  *B29K 105/00*  (2006.01)

(56) References Cited

FOREIGN PATENT DOCUMENTS

| | | |
|---|---|---|
| KR | 10-2010-0049341 A | 5/2010 |
| KR | 10-2017-0012099 A | 2/2017 |
| WO | WO 2018/071639 A1 | 4/2018 |
| WO | WO 2018071639 * | 4/2018 |

* cited by examiner

HYDROGEL COMPOSITION AND BIOINK COMPOSITION INCLUDING THE SAME

CROSS-REFERENCE TO RELATED APPLICATION

This application claims the benefit of Korean Patent Application No. 10-2018-0117871, filed on Oct. 2, 2018, in the Korean Intellectual Property Office, the disclosure of which is incorporated herein in its entirety by reference.

BACKGROUND

1. Field

One or more embodiments relate to a hydrogel composition having high viscoelasticity and a bioink composition including the same.

2. Description of the Related Art

Three-dimensional printing refers to fabricating a complex skeletal structure by a layer-by-layer process after conversion of configuration information derived from medical data of tissues or organs having complex configurations into G-code. Such three-dimensional printing is also referred to as 'three-dimensional bioprinting (3D bioprinting)'. Typically, biocompatible polymeric hydrogels are loaded into piston syringes, so as to prepare a three-dimensional structure.

Hydrogels have excellent hydrophilicity, and thus may be able to absorb water easily. In addition, the strength and shape of hydrogels are easily changed, and thus hydrogels are used as supports in tissue engineering or used for drug delivery. Due to the hydrophilic nature of their constituents, hydrogels may swell by absorbing a large amount of water in an aqueous solution or an aqueous environment. However, due to their cross-linking structure, hydrogels do not dissolve. Therefore, depending on constituents and a fabricating method, hydrogels with various shapes and properties may be fabricated. Hydrogels containing a large amount of water are generally characterized by their intermediate nature between liquid and solid.

Meanwhile, gelatin is a protein that is widely used as a biocompatible polymer of hydrogels and is obtained by partial hydrolysis of collagen, which is a main protein component of connective tissues such as animal bones, cartilage, and leather. In this regard, gelatin has high biocompatibility and non-toxic biodegradability. Gelatin provides viscosity at a relatively low temperatures and a relatively low concentration. When a gelatin-containing solution is cooled, a clear and elastic thermoreversible gel is formed. However, since such a thermoreversible gel easily dissolves in an aqueous solution, a cross-linking method using a chemical substance, such as formaldehyde or glutaraldehyde, is applied in order to improve stability of the thermoreversible gel. However, when a cross-linking agent remains in trace amounts in the thermoreversible gel, the thermoreversible gel may exhibit not only cytotoxicity, but also toxicity to the surrounding organs after transplantation.

Accordingly, the inventors of the present disclosure have studied a hydrogel composition having high viscosity without a chemical cross-linking agent. As a result, a hydrogel composition having high viscosity with critical significance has been developed by mixing natural biocompatible polymers at a certain concentration, and the present disclosure is completed by confirming application of the hydrogel composition in 3D bioprinting.

SUMMARY

One or more embodiments include a hydrogel bioink composition for bioprinting including 10% by weight or more of collagen with respect to the total amount of the composition.

One or more embodiments include a composition for use as a bone tissue injecting material and a soft tissue filler, the composition including 10% by weight or more of collagen with respect to the total amount of the composition.

One or more embodiments include a bioink composition for bioprinting including: collagen or gelatin in an amount of 0.2% by weight to 6% by weight; and hyaluronic acid in an amount of 2% by weight to 8% by weight, with respect to the total amount of the bioink composition.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
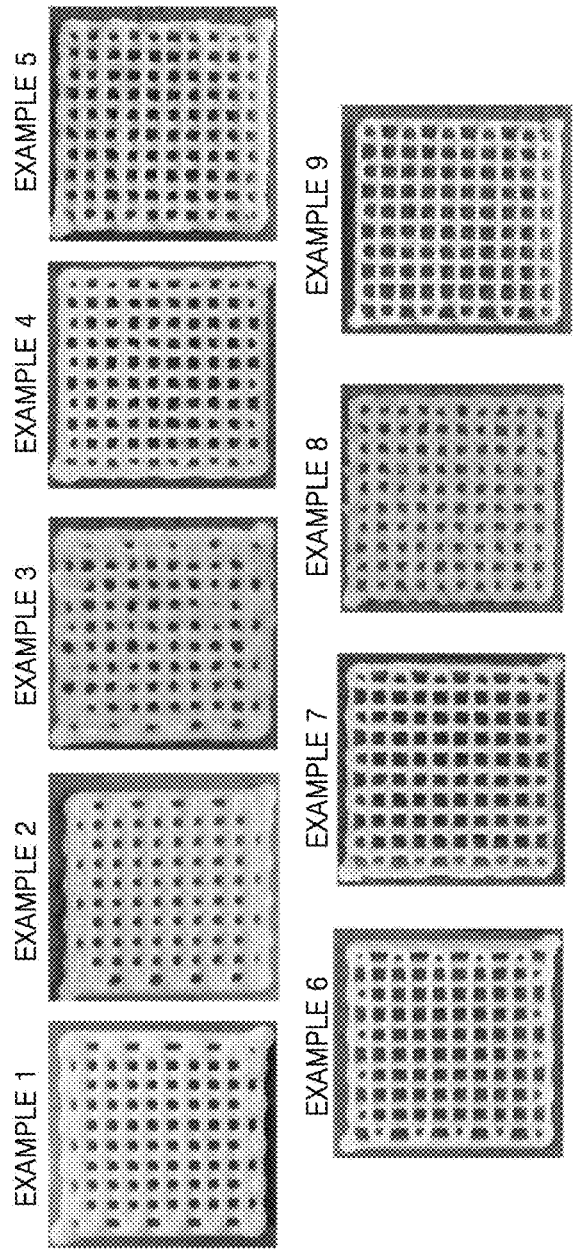
FIG. 1A shows images of printed bioink composition according to Examples.
Figure 1B:
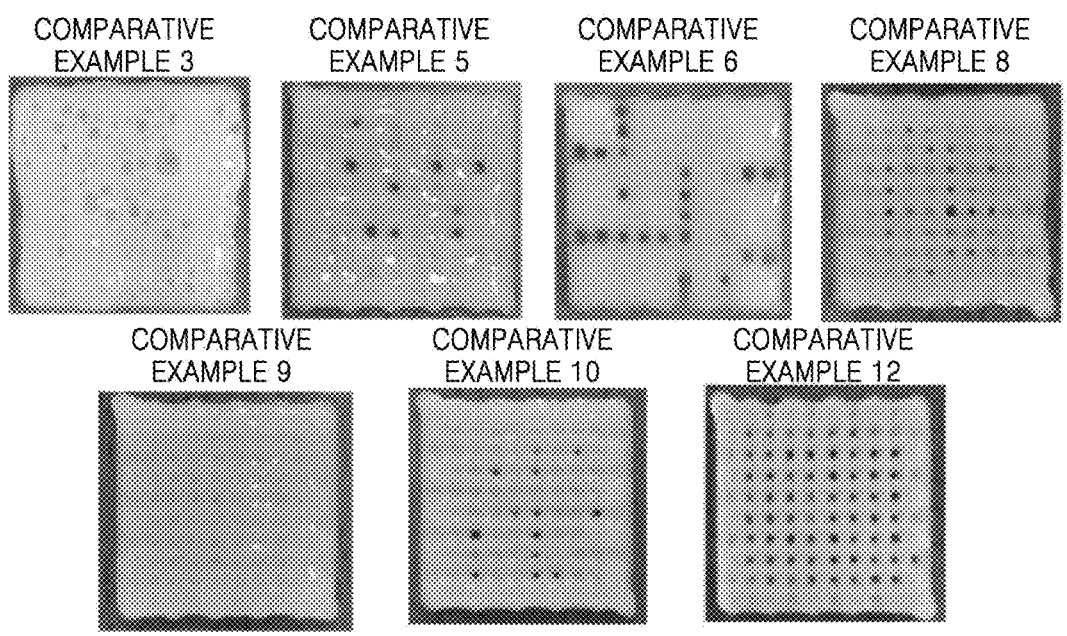
FIG. 1B shows images of printed bioink composition according to Comparative Examples.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Additional aspects will be set forth in part in the description which follows and, in part, will be apparent from the description, or may be learned by practice of the presented embodiments.

An aspect of the present disclosure provides a hydrogel composition including 10% by weight or more of collagen with respect to the total amount of the hydrogel composition.

Another aspect of the present disclosure provides a tissue engineering support or a bioink composition including 10% by weight or more of collagen.

The term "hydrogel" as used herein refers to a three-dimensional network of hydrophilic polymers that are cross-linked via covalent or non-covalent bonds. Due to the hydrophilic nature of hydrogel constituents, hydrogels swell by absorbing a large amount of water in an aqueous solution or an aqueous environment, but do not dissolve because of a cross-linking structure thereof. Therefore, depending on constituents and a fabricating method, hydrogels with various shapes and properties may be prepared. Hydrogels containing a large amount of water are generally characterized by the intermediate nature of liquids and solids.

The term "bioink" as used herein refers to a hydrogel or a mixture of cells with a hydrogel used for bioprinting. Therefore, a bioink composition may be applied for bioprinting. In addition, the bioink composition may be a hydrogel, and more particularly, may be applied for skin generation.

In one embodiment, the bioink composition may include 10% by weight of collagen. For example, the amount of the collagen may be in a range of 10% by weight to 90% by weight, 10% by weight to 80% by weight, 10% by weight to 70% by weight, 10% by weight to 60% by weight, 10% by weight to 50% by weight, 10% by weight to 40% by weight, 10% by weight to 30% by weight, or 10% by weight to 20% by weight. Here, when the ratio of the collagen is less than the ranges above, the bioink may not be produced homogeneously, and accordingly, there is a problem of maintaining the shape fidelity of a printed structure using the bioink. In addition, when the ratio of the collagen exceeds the ranges above, the collagen also exceeds the maximum solubility thereof, and accordingly, the collagen may not be prepared in a solution form. In general, when 6% by weight or more of a collagen solution is rapidly neutralized, a collagen gel may not be formed homogeneously. Thus, by using a dual syringe, 6% by weight of the collagen solution on one side and a neutralization buffer on the other side are used as injections. However, when 10% by weight or more of the collagen in the bioink composition according to an embodiment is slowly subjected to gelation in an ice state, a collagen gel may be formed homogeneously. In this regard, there is an advantage that a homogeneous bioink may be produced.

In one or more embodiments, the bioink composition may include hyaluronic acid in an amount of 1% by weight to 8% by weight. For example, the amount of the hyaluronic acid may be in a range of 1% weight to 8% by weight, 1% by weight to 6% by weight, 1% by weight to 4% by weight, 1% by weight to 3% by weight, 2% by weight to 6% by weight, or 2% by weight to 5% by weight. Here, when the ratio of the hyaluronic acid is less than the ranges above, the hyaluronic acid fails to sufficiently increase the viscosity of the bioink composition, and when the ratio of the hyaluronic acid exceeds the ranges above, there is a problem that the viscosity of the bioink may be significantly reduced.

The term "hyalruronic acid" as used herein is used interchangeably with "hyaluronan", "hyaluronate", or "HA", and may be represented by Formula 1 and include a pharmaceutically acceptable thereof, such as sodium hyaluronate (NaHA), potassium hyaluronate, magnesium hyaluronate, or a combination of potassium hyaluronate and a foregoing salt.

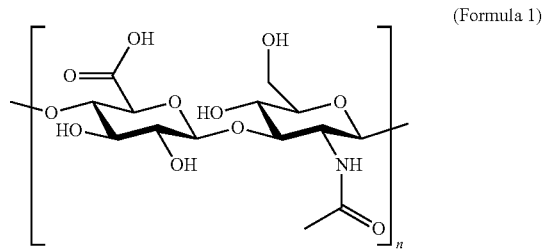

(Formula 1)

In Formula 1, n indicates the number of a repeating unit. Hyaluronic acid of all origins including bacteria and algae is useful. Such useful hyaluronic acid may be used in a molecular weight range of about 0.3 MDa to about 6.0 MDa, for example, about 1.5 MDa to about 6.0 MDa, about 2.5 MDa to about 6.0 MDa, about 3.5 MDa to about 6.0 MDa, about 0.3 MDa to about 5.0 MDa, about 0.3 MDa to about 4.0 MDa, or about 0.3 MDa to about 3.0 MDa.

In one or more embodiments, the composition may include fibrinogen in an amount of about 1% by weight to about 15% by weight. For example, the amount of fibrinogen may be in a range of about 1% by weight to about 15% by weight, 1% by weight to about 12% by weight, about 1% by weight to about 10% by weight, about 1% by weight to about 8% by weight, about 1% by weight to about 6% by weight, about 1% by weight to about 4% by weight, or about 1% by weight to about 2% by weight. Here, when the amount of fibrinogen is less than the ranges above, fibrinogen fails to sufficiently perform the function of increasing the yield stress, and when the amount of fibrinogen is greater than the ranges above, the yield stress of the composition is excessively increased.

The term "fibrinogen" as used herein refers to a glycoprotein in vertebrates, and may serve as a cross-linking agent. Thus, in the hydrogel composition, the tissue-engineering support composition, or the bioink composition according to an embodiment, the composition is subjected to gelation by itself at a temperature ranging from about 20° C. to about 37° C. and a pH ranging from about 6.5 to about 7.5 so that an additional cross-linking agent, e.g., a chemical cross-linking agent, may not be substantially included. In general, cross-linking agent is added to improve or increase gelation or viscoelasticity. In this regard, in the composition according to an embodiment, the fibrinogen not only has a role of increasing the yield stress, but also has an advantage of being able to maintain the shape to be suitable for printing or injection by including collagen at a high concentration.

The expression "does not contain", "is free of", or "substantially free of" as used herein indicates that a cross-linking agent, e.g., a chemical cross-linking agent, is not included in an effective amount, i.e., it is present in an amount insufficient to perform its complete role. In detail, the amount of the cross-linking agent is less than about 1% by weight, less than about 0.5% by weight, less than about 0.1% by weight, or in one or more embodiments, less than about 0.05% by weight or the like, with respect to the total amount of the composition, or may be absent from the composition.

In one or more embodiments, the composition may include hyaluronic acid in a range of about 1 by weight to about 8% by weight and fibrinogen in a range of about 1% by weight to about 15% by weight. The hyaluronic acid and the fibrinogen are each the same as defined above.

In one or more embodiments, the composition may further include thrombin. Fibrinogen may be cross-linked by an enzymatic reaction, and the thrombin may then convert fibrinogen into fibrin, thereby reducing the rate of gelation and decomposition/absorption of the composition.

In one or more embodiments, the composition may be a cell-laden composition. In addition, the composition may further include a growth factor or a differentiation factor. The cells included in the composition may include cells to be cultured in the hydrogel composition, tissues, or cells to be differentiated into other cells, or cells to be used for tissue regeneration. Examples of the cells are stem cells, sensory cells, brain cells, germ cells, epithelial cells, immune cells, cartilage cells, bone cells, cancer cells, or combinations thereof. The stem cells may refer to cells having differentiation potency, and examples thereof are blast cells, hepatocytes, fibroblasts, myoblasts, adult stem cells, mesenchymal stem cells, adipose-derived mesenchymal stem cells, bone marrow-derived mesenchymal stem cells, nerve-derived mesenchymal stem cells, placenta-derived mesenchymal stem cells, cord blood stem cells or combinations thereof. The growth factor may refer to a substance capable of regulating the growth and function of a cell. The differentiation factor may refer to a substance that induces differentiation of cells into tissues or other cells. For example, the growth factor or the differentiation factor may include a transformed growth factor (TGF), a vascular endothelial growth factor (VEGF), a fibroblast growth factor (FGF), an epithelial growth factor (EGF), a platelet-derived growth factor (PDGF), a hepatocyte growth factor (HGF), an insulin-like growth factor (IGF), a cytokine, a chemokine, or combinations thereof.

In one embodiment, the composition may have an elastic modulus in a range of about 3,000 Pa to about 10,000 Pa. For example, the composition may have an elastic modulus in a range of about 3,000 Pa to about 10,000 Pa, about 3,000 Pa to about 9,000 Pa, about 3500 Pa to about 8,000 Pa, about 4,000 Pa to about 8,000 Pa, about 5,000 Pa to about 7,500 Pa, or about 5,500 Pa to about 6,500 Pa. In addition, the composition may have a viscosity value of at least about 25,000, at least about 30,000, at least about 40,000, at least about 50,000, or at least about 60,000 cP. In detail, the composition may have a viscosity value in a range of about 25,000 to about 2,000,000 cP, about 30,000 to about 1,500,000 cP, about 40,000 to about 6,000,000 cP, about 40,000 to about 1,000,000 cP, about 50,000 to about 200,000 cP, about 60,000 to about 200,000 cP, or about 70,000 to about 180,000 cP. The viscosity may be measured prior to gelation using a rheometer at a specific temperature in a range of about 20° C. to about 40° C., for example, about 25° C. or 30° C.

Another aspect of the present disclosure provides an injectable composition for bone tissues and a soft tissue filler composition, each including the hydrogel composition. The hydrogel composition including the collagen is the same as defined above.

The composition may include a therapeutically effective amount of at least one anesthetic, for example, lidocaine or the like.

The composition according to an embodiment is biocompatible and has a high viscosity characteristic. In this regard, the composition may be able to induce tissue regeneration of cells in a semi-permanent manner, and thus, may be usefully utilized as a tissue filler. In addition, for example, the composition may last for at least 3 months, at least 6 months, or at least 1 year after being introduced into the skin.

Another aspect of the present disclosure provides a method of preparing a biocompatible structure, the method including: preparing a bioink composition including 10% by weight or more of collagen with respect to the total amount of the hydrogel bioink composition; and preparing a support by subjecting the hydrogel bioink composition to 3D printing. The bioink composition is the same as defined above.

The term "biocompatible structure" as used herein refers to a structure that is substantially non-toxic to the human body, is chemically inert, and has no immunogenicity. Such a biocompatible structure may be fabricated into a three-dimensional fine-structured artificial organ by using a bio-printer, a scaffold (i.e., a bio-support), or a drug carrier.

The method according to an embodiment may further include plotting cells on a support for printing. Here, an amount of the cells may be in a range of about 0.5% by weight to about 10% by weight, about 1% by weight to about 5% by weight, or about 1% by weight to about 3% by weight, with respect to the total amount of the hydrogel bioink composition. The 3D printed support may have an arrangement in which a plurality of horizontal lines arranged in horizontal direction and a plurality of vertical lines arranged in a vertical direction cross each other in a network structure. The network structure may have a plurality of holes, and may be printed in a layering manner in which the cells are repeatedly filled in the plurality of holes. The printing may be repeatedly performed 2 times to 10 times, 2 times to 9 times, 2 times to 8 times, 2 times to 7 times, 2 times to 6 times, 3 times to 8 times, 4 times to 8 times, 4 times to 7 times, or 5 times to 7 times. The cells are the same as defined above.

In addition, the support may further include a drug. Here, an amount of the drug may be in a range of about 0.5% by weight to about 10% by weight, about 1% by weight to about 5% by weight, or about 1% by weight to about 3% by weight, with respect to the total amount of the hydrogel bioink composition. When the amount of the drug is less than the range above, the drug may not be efficiently delivered to a target site, and when the amount of the drug is greater than the range above, the drug may not be efficiently loaded on the bioink. Considering that the drug needs to be loaded on the bioink to be efficiently delivered to a target site, a drug release speed may be effectively controlled. In addition, for use as the drug, a variety of substances may be used depending on a target site, a therapeutic purpose, and the like. In detail, the drug may be an anti-cancer agent, an anti-inflammatory agent, and the like. For example, the drug may be an anti-inflammatory agent selected from: paclitaxel, doxorubicin, retinoic acid and the like, cis-platin, camptothecin, 5-FU, Docetaxel, Tamoxifen, anasterozole, carboplatin, topotecan, belotecan, irinotecan, gleevec, and vincristine; or aspirin, salicylates, ibuprofen, naproxen, fenoprofen, indomethacin, phenylatazone, methotrexate, cyclophosphamide, mechlorethamine, dexamethasone, prednisolone, celecoxib, valdecoxib, nimesulide, cortisone, and corticosteroid.

Another aspect of the present disclosure provides a hydrogel composition including collagen or gelatin; hyaluronic acid; and/or fibrinogen. Another aspect of the present disclosure provides a tissue-engineering support or a bioink composition including collagen or gelatin; hyaluronic acid; and/or fibrinogen. Another aspect of the present disclosure provides a soft tissue filler composition including the hydrogel composition. The hydrogel composition including collagen or gelatin; hyaluronic acid; and/or fibrinogen is the same as defined above.

Another aspect of the present disclosure provides a method of preparing a biocompatible structure, the method including: preparing a bioink composition including collagen or gelatin in a range of about 0.2% by weight to about 6% by weight and hyaluronic acid in a range of about 2% by weight to about 8% by weight with respect to the total amount of the bioink composition; and preparing a support by subjecting the bioink composition to 3D printing. The method of the biocompatible structure is the same as defined above.

Hereinafter, example embodiments will be described in further detail with reference to the following examples and comparative examples. However, these examples are provided for illustrative purposes only and are not intended to limit the scope of the present disclosure.

EXAMPLES

Examples 1 to 9: Preparation of Bioink Composition

To prepare each of bioink compositions, collagen (Sewon Cellontech, Korea) or hyaluronic acid (Contipro, France, supplied by Huons, Korea), and/or fibrinogen (MP Biomedicals, USA) were used.

In detail, hyaluronic acid was dissolved in DPBS containing $CaCl_2$ (to a final concentration of 50 mM), and then, mixed with a collagen solution at a ratio of 1:1 at a temperature of 4° C. Afterwards, 1N NaOH was added thereto to neutralize the mixed solution, and the resulting solution was immediately mixed with fibrinogen. A thrombin solution (100 IU/ml in PBS) was added thereto to produce a bioink composition having a final concentration of 1 IU/ml. Amounts (% by weight) of collagen, hyaluronic acid, and/or fibrinogen in the prepared bioink composition are shown in Table 1.

TABLE 1

| No. | Collagen (% by weight) | Hyaluronic acid (% by weight) | Fibrinogen (% by weight) |
| --- | --- | --- | --- |
| Example 1 | 10 | 0 | 0 |
| Example 2 | 10 | 2.5 | 0 |
| Example 3 | 10 | 2.5 | 8 |
| Example 4 | 16 | 0 | 4 |
| Example 5 | 16 | 2 | 3 |
| Example 6 | 18 | 0 | 0 |
| Example 7 | 18 | 0 | 2 |
| Example 8 | 18 | 2.5 | 2 |
| Example 9 | 20 | 5 | 0 |

Examples 10 to 36: Preparation of a Bioink Composition

Bioink compositions were each prepared in the same manner as in Examples 1 to 9, except that hyaluronic acid was dissolved in DPBS containing $CaCl_2$ (to a final concentration of 50 mM), and then, mixed with a collagen or gelatin solution (Sigma-Aldrich, CA, USA) at a ratio of 1:1 at a temperature of 4° C. Amounts (% by weight) of collagen, gelatin, hyaluronic acid, and/or fibrinogen in the prepared bioink composition are shown in Table 2.

TABLE 2

| No. | Collagen (% by weight) | Gelatin (% by weight) | Hyaluronic acid (% by weight) | Fibrinogen (% by weight) |
| --- | --- | --- | --- | --- |
| Example 10 | 0.5 | 0 | 1.25 | 0 |
| Example 11 | 0.5 | 0 | 1.25 | 5 |
| Example 12 | 0.5 | 0 | 1.25 | 10 |
| Example 13 | 0.5 | 0 | 1.25 | 20 |
| Example 14 | 0.5 | 0 | 2.5 | 0 |
| Example 15 | 0.5 | 0 | 2.5 | 5 |
| Example 16 | 0.5 | 0 | 2.5 | 10 |
| Example 17 | 0.5 | 0 | 2.5 | 20 |
| Example 18 | 0.5 | 0 | 5 | 0 |
| Example 19 | 0.5 | 0 | 5 | 5 |
| Example 20 | 0.5 | 0 | 5 | 10 |
| Example 21 | 0.5 | 0 | 5 | 20 |
| Example 22 | 0.25 | 0 | 5 | 0 |
| Example 23 | 0.25 | 0 | 5 | 5 |
| Example 24 | 0.25 | 0 | 5 | 10 |
| Example 25 | 0.25 | 0 | 5 | 20 |
| Example 26 | 0 | 0 | 5 | 0 |
| Example 27 | 0 | 0 | 5 | 5 |
| Example 28 | 0 | 0 | 5 | 10 |
| Example 29 | 0 | 0 | 5 | 20 |
| Example 30 | 0 | 0.25 | 5 | 0 |
| Example 31 | 0 | 0.5 | 5 | 0 |
| Example 32 | 0 | 1 | 5 | 0 |
| Example 33 | 0 | 2 | 5 | 0 |
| Example 34 | 0 | 3 | 5 | 0 |
| Example 35 | 0 | 4 | 5 | 0 |
| Example 36 | 0 | 5 | 5 | 0 |

COMPARATIVE EXAMPLES

Comparative Examples 1 to 13: Preparation of a Bioink Composition

Bioink compositions were each prepared in the same manner as in Examples 1 to 9, except that the following compositional ratios in Table 3 were used.

TABLE 3

| No. | Collagen (% by weight) | Hyaluronic acid (% by weight) | Fibrinogen (% by weight) |
| --- | --- | --- | --- |
| Comparative Example 1 | 0 | 0 | 10 |
| Comparative Example 2 | 0 | 2.5 | 10 |
| Comparative Example 3 | 2 | 0 | 0 |
| Comparative Example 4 | 2 | 0 | 8 |
| Comparative Example 5 | 2 | 1.25 | 4 |
| Comparative Example 6 | 2 | 2.5 | 0 |
| Comparative Example 7 | 2 | 2.5 | 8 |
| Comparative Example 8 | 5 | 0 | 5 |
| Comparative Example 9 | 5 | 2.5 | 5 |
| Comparative Example 10 | 6 | 1.25 | 0 |
| Comparative Example 11 | 6 | 1.25 | 8 |
| Comparative Example 12 | 8 | 0 | 2 |
| Comparative Example 13 | 8 | 2.5 | 2 |

EXPERIMENTAL EXAMPLES

Experimental Example 1. Characteristic Analysis of Bioink Composition 1-1. Analysis of Elasticity and Yield Stress of Bioink Composition The elasticity of each of the bioink compositions prepared according to Examples 1 to 9 and Comparative Examples 1 to 13 was measured by using a rotational rheometer (AR-G2, TA instrument Ltd., DE, USA). In detail, each of the bioink compositions was placed on a parallel plate of the rheometer, and then, a storage modulus (G') was measured at a temperature of 20° C. for 20 minutes on a fixed strain (0.1%) at a frequency of 1 rad/s. In addition, to measure the yield stress, a sheer stress applied to the bioink was increased and the point where the viscosity is rapidly decreased while the sheer stress rate is rapidly increased measured as a yield stress. For the elasticity, the elastic modulus at the frequency of 1 rad/s was defined as the representative elasticity value. The yield stress and elasticity measurements are shown in Table 4

TABLE 4

| No. | Elasticity (Pa) | Yield stress(Pa) |
| --- | --- | --- |
| Example 1 | 3620 | 632 |
| Example 2 | 2260 | 430 |
| Example 3 | 4380 | 5506 |
| Example 4 | 8043 | 1645 |
| Example 5 | 3921 | 1323 |
| Example 6 | 9372 | 1465 |
| Example 7 | 6949 | 1334 |
| Example 8 | 5257 | 1528 |
| Example 9 | 9953 | 532 |
| Comparative Example 1 | 7761 | 50000 |
| Comparative Example 2 | 1888 | 10855 |
| Comparative Example 3 | 382 | 282 |
| Comparative Example 4 | 1693 | 9400 |
| Comparative Example 5 | 460 | 770 |
| Comparative Example 6 | 230 | 74 |
| Comparative Example 7 | 1327 | 3960 |
| Comparative Example 8 | 1112 | 3130 |
| Comparative Example 9 | 731 | 541 |
| Comparative Example 10 | 820 | 226 |
| Comparative Example 11 | 4572 | 8052 |
| Comparative Example 12 | 1295 | 730 |
| Comparative Example 13 | 1122 | 415 |

As shown in Table 4, it was found that the bioink compositions prepared according to Examples 1 to 9 had high elastic characteristics and high yield stress with critical significance as compared with those of the bioink compositions prepared according to Comparative Examples 1 to 13. In this regard, the bioink compositions prepared according to Examples 1 to 9 may be retained in a constant shape, thereby enabling to form a cell-laden structure.

Figure 2:
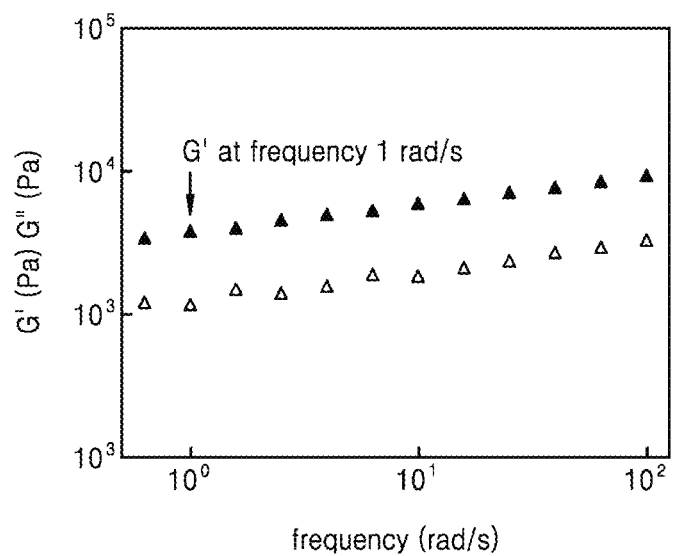
FIG. 2 is a graph showing the results of elastic modulus measurements obtained in Example 1.
Figure 3:
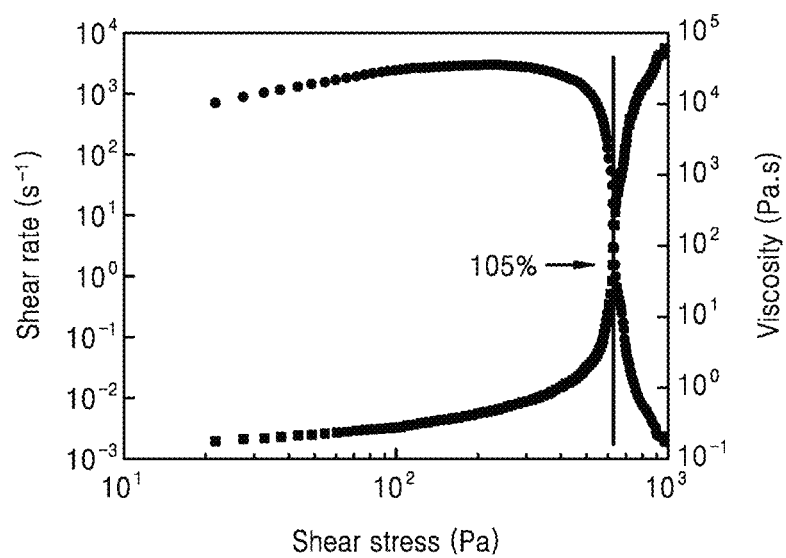
FIG. 3 is a graph showing the results of yield stress measurements obtained in Example 1.

FIG. 2 is a graph showing the results of elastic modulus measurements obtained in Example 1. As shown in FIG. 2, the elastic modulus of the bioink compositions prepared according to Examples 1 to 9 showed gelation behavior showing almost parallel values regardless of the frequency. FIG. 3 is a graph showing the results of yield stress measurements obtained in Example 1. As shown in FIG. 3, it was confirmed that the bioink compositions prepared according to Examples 1 to 9 each had a yield stress within a measurable range.

1-2. Analysis of Viscosity of Bioink Composition

The viscosity of each of the bioink compositions prepared according to Examples 10 to 36 was measured at a temperature of 25° C. by using a Brookfield digital rheometer (Model DV-III, Brookfield Engineering Lab., Inc., MA, USA), and the results are shown in Table 5. In addition, the viscosity of each of the bioink compositions prepared according to Examples 32 to 36 was measured, and the results are shown in Table 6.

TABLE 5

| No. | Viscosity (cP) |
| --- | --- |
| Example 10 | 12,000 ± 3,600 |
| Example 11 | 19,000 ± 3,000 |
| Example 12 | — |
| Example 13 | — |
| Example 14 | 15,000 ± 3,200 |
| Example 15 | 25,000 ± 3,200 |
| Example 16 | 27,000 ± 3,200 |
| Example 17 | 63,000 ± 4,400 |
| Example 18 | 37,000 ± 4,500 |
| Example 19 | 76,000 ± 6,900 |
| Example 20 | 180,000 ± 17,600 |
| Example 21 | 880,000 ± 44,900 |
| Example 22 | 19,000 ± 1,600 |
| Example 23 | 33,000 ± 3,000 |
| Example 24 | 56,000 ± 4,000 |
| Example 25 | — |
| Example 26 | 11,000 ± 2,800 |
| Example 27 | 17,000 ± 3,000 |
| Example 28 | 36,000 ± 2,700 |
| Example 29 | — |
| Example 30 | — |
| Example 31 | 19,000 ± 1,600 |
| Example 32 | 34,000 ± 3,900 |
| Example 33 | 620,000 ± 5,100 |
| Example 34 | 1,450,000 ± 128,000 |
| Example 35 | 3,440,000 ± 123,000 |
| Example 36 | 5,970,000 ± 102,000 |

TABLE 6

| No. | Viscosity (cP) |
| --- | --- |
| Bioink 22 | 16,000 ± 3,200 |
| Bioink 23 | 21,000 ± 3,500 |
| Bioink 24 | 62,000 ± 3,900 |
| Bioink 25 | 73,000 ± 3,700 |
| Bioink 26 | 380,000 ± 36,000 |
| Bioink 27 | 1,470,000 ± 120,000 |

As shown in Tables 5 and 6, it was confirmed that the bioinks including collagen or gelatin in a range of about 0.2% by weight to about 6% by weight; hyaluronic acid in a range of about 2% by weight to about 8% by weight; and/or fibrinogen in a range of about 2% by weight to about 25% by weight had high viscosity characteristics with critical significance as compared with those of other bioinks.

1-3. Analysis of Viscoelaticity of Bioink Composition

The viscoelasticity of each of the bioink compositions prepared according to Examples 10 to 36 was measured by using a rotational rheometer (AR-G2, TA instrument Ltd., DE, USA). In detail, each of the bioinks was placed on a parallel plate of the rheometer, and then, a storage modulus G' and a loss modulus (G") were each measured at a temperature of 37° C. for 20 minutes on a fixed strain (0.1%) at a frequency of 1 rad/s.

Figure 4:
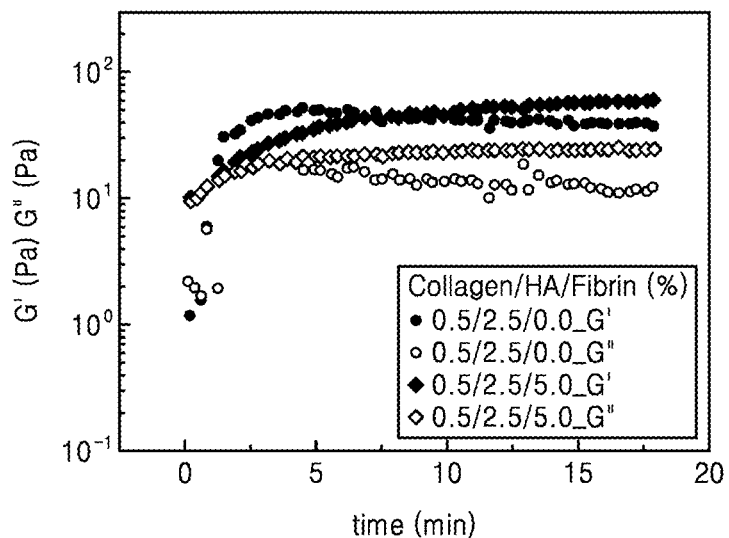
FIG. 4 is a graph showing viscoelasticity of a bioink composition according to an embodiment.

Among the three components, i.e., collagen, hyaluronic acid, and fibrinogen, the concentration of fibrinogen was a variable while the concentrations of the remaining components were fixed with 0.5% (collagen) and 2.5% (hyaluronic acid), for the measurement performed in Examples 14 and 15, and the results are shown in FIG. 4.

FIG. 4 is a graph showing viscoelasticity of a bioink composition according to an embodiment.

As shown in FIG. 4, it was confirmed that G' (referring to the elastic modulus) and G" (referring to the viscosity coefficient) increased with time. As such, the fact that G' is greater than G" indicates that the blink has a gel-type shapel.

1-4. Analysis of Printability of Bioink Composition

The printability of each of the bioink compositions prepared according to Examples 1 to 9, 15, 19, and 20 and Comparative Examples 1 to 13 was measured by using an extrusion-based bioprinting device (Biobot1, BioBots, PA, USA). In detail, each of the bioinks was added to a syringe barrel, and then, loaded into a bio-printer to analyze the printability. In addition, each of the bioink compositions prepared according to Examples 1 to 9 and Comparative Examples 1 to 13 was used for a 3D Bio printer (manufactured by Korea Institute of Machinery and Materials) or used in vivo (Rokit) to be printed. Afterwards, the printed pattern was measured by using the Image J software to measure the shape fidelity according to Equation 1 below, and the results are shown in Table 4.

$$\text{Shape fidelity} = \text{Area of empty space}/\text{total area} = 1 - (\text{area of printing pattern}/\text{total area}) \quad \text{[Equation 1]}$$

TABLE 7

| No. | Shape fidelity | Extrusion |
|---|---|---|
| Example 1 | 14.6 | 1 |
| Example 2 | 12.61 | 1 |
| Example 3 | 14.08 | 1 |
| Example 4 | 22.9 | 1 |
| Example 5 | 23.55 | 1 |
| Example 6 | 31.27 | 1 |
| Example 7 | 33.66 | 1 |
| Example 8 | 19.61 | 1 |
| Example 9 | 41.74 | 1 |
| Comparative Example 1 | — | 0 |
| Comparative Example 2 | — | 0 |
| Comparative Example 3 | 0 | 1 |
| Comparative Example 4 | — | 0 |
| Comparative Example 5 | 1.08 | 1 |
| Comparative Example 6 | 4.94 | 1 |
| Comparative Example 7 | — | 0 |
| Comparative Example 8 | 0.47 | 1 |
| Comparative Example 9 | 0 | 1 |
| Comparative Example 10 | 0.7 | 1 |
| Comparative Example 11 | — | 0 |
| Comparative Example 12 | 7.34 | 1 |
| Comparative Example 13 | 0.13 | 1 |

*Extrusion: 0, nozzle blocking

As shown in Table 7, it was confirmed that each of the bioink compositions prepared according to Examples 1 to 9 had excellent shape fidelity and showed no nuzzling blockage as compared with the bioink compositions prepared according to Comparative Examples 1 to 13.

Figure 5:
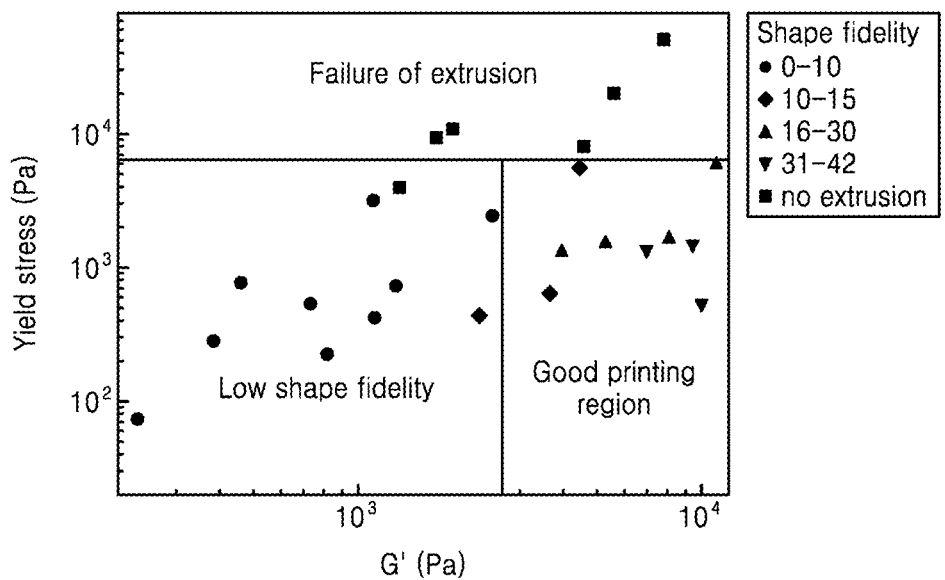
FIG. 5 is a graph confirming a good printing region based on yield stress and elastic modulus values.

FIG. 5 a graph confirming an area where printing was good according to yield stress and elastic modulus values. As shown in FIG. 5, when the modulus value (G') was large and the yield stress value was small, the presence of the area where printing was good was confirmed.

Figure 6:
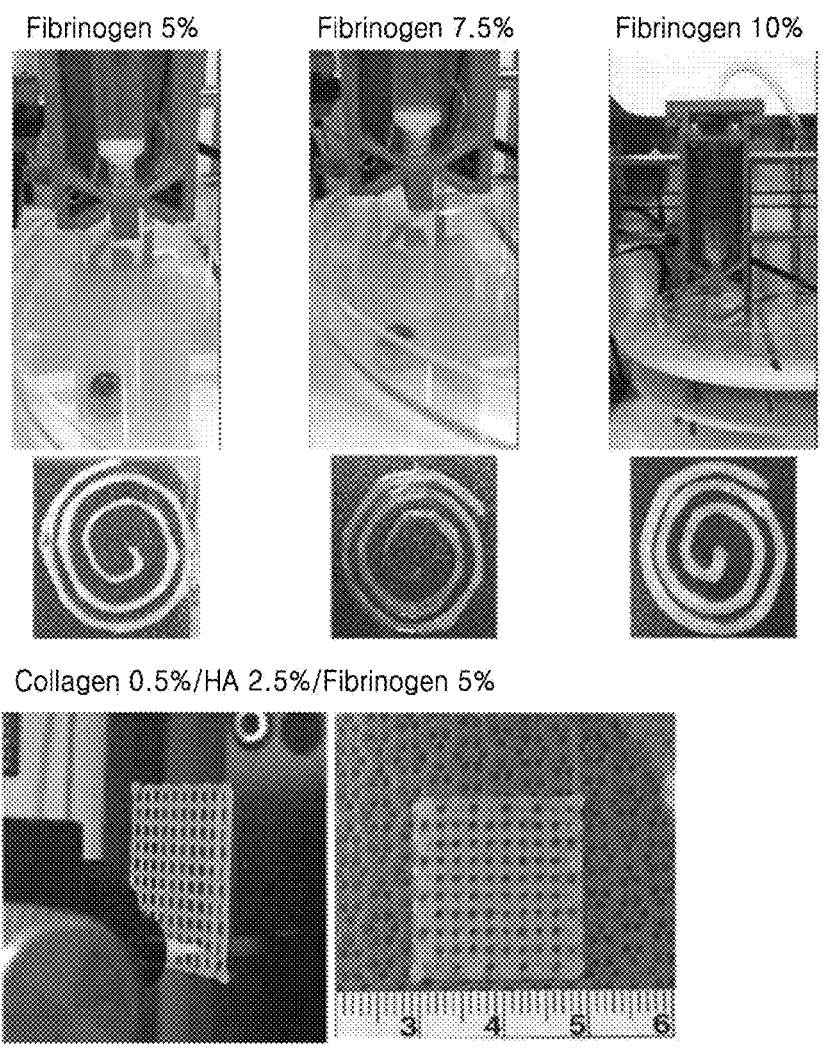
FIG. 6 shows images of printing characteristics of a bioink composition according to an embodiment.

FIG. 6 shows images of printing characteristics of a bioink composition according to an embodiment. As shown in FIG. 6, it was confirmed that the bioink composition according to an embodiment showed an appropriate viscosity value so that may be printed within a uniform thickness.

The bioink composition including collagen in an amount of at least 10% by weight was found to have excellent elasticity characteristics so that the bioink composition had the shape fidelity. That is, the bioink composition may form a laminate, and due to the yield stress with the critical significance, the nozzle blocking in a printing environment may be prevented.

1-3. Analysis of Viability of Cells in a Printing Support

The viability of fibroblasts in a printing support of the bioink was observed. In detail, the bioink prepared according to Example 6 was used with a 3D Bio printer (Korea Institute of Machinery and Materials) for printing a support. Afterwards, an empty space in the support was filled with a mixture of fibroblasts and low-concentrated bioink by a printing process. Here, the low-concentrated bioink contained 1% by weight of collgen. A cycle of printing one layer on the support and subsequently filling empty spaces of the printed layer with a mixture of cells and a hydrogel was repeated layer-by-layer, thereby layering a total of 6 layers on the support. Immediately after the printing, the support was stabilized at a temperature of 37° C. for 1 hour, and cells in the support were cultured for 7 days in a cell culture medium (supplemented with DMEM high Glucose+10% FBS+1% penicillin streptomycin). After 7 days, by using a LIVE/DEAD® Reduced Biohazard Viability/Cytotoxicity Kit (SYTO 10, ethidium homodimer-2, manufactured by Molecular probes Company), the cells were stained for 1 hour, and then, fixed with 4% paraformaldehyde. Then, the cell viability was observed with a confocal microscope.

Figure 7A:
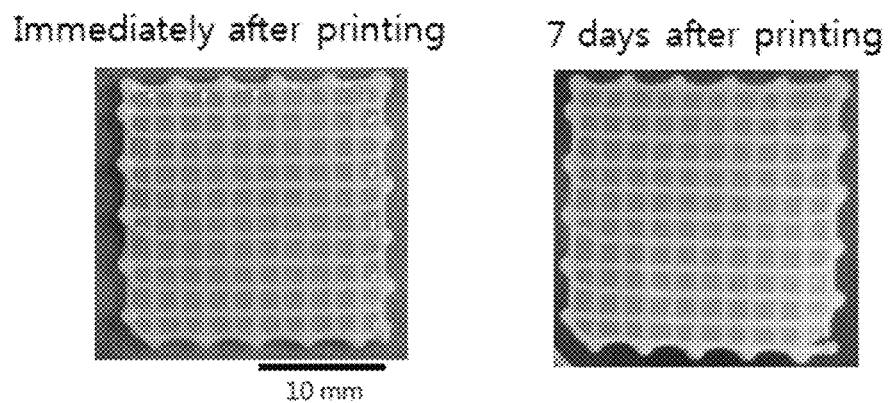
FIG. 7A shows an image of printed bioink composition immediately after printing with injection of 1% collagen and fibroblasts and an image showing changes in the printed bioinks 7 days after the printing.
Figure 7B:
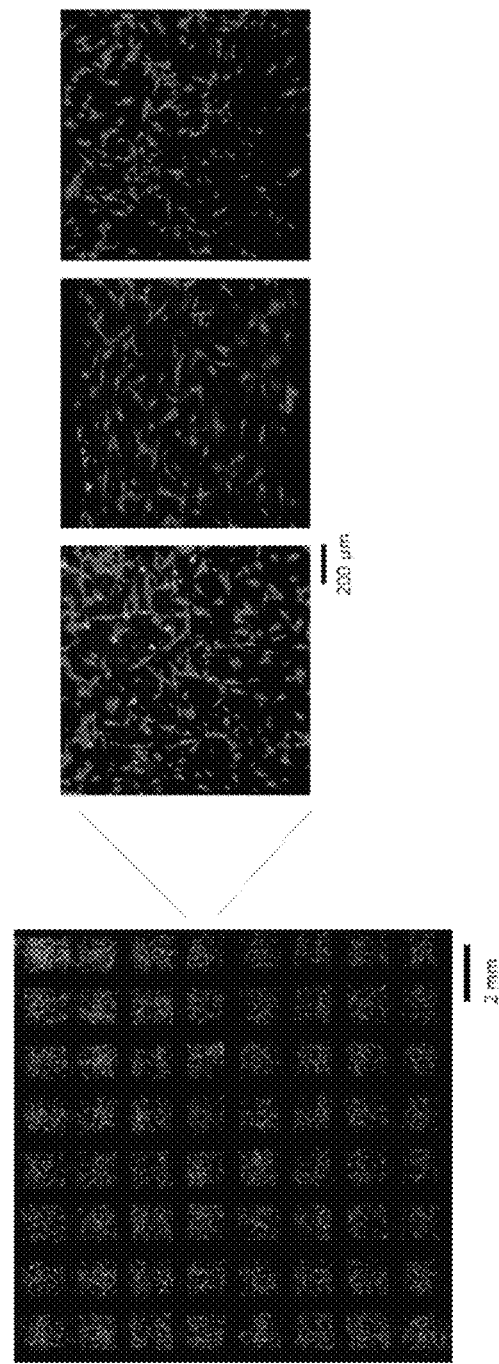
FIG. 7B is an image showing cell viability in the printed bioink composition at 7 days after printing.

FIG. 7A shows an image obtained immediately after the printing by injection of the bioink of Example 6 and a mixture of 1% collagen and fibroblasts and an image showing changes 7 days after printing, and FIG. 7B is an image showing the cell viability 7 days after printing.

As shown in FIG. 7A, it was confirmed that the cell-laden support exhibit the shape fidelity without showing any shrinkage or decomposition. In addition, as shown in FIG. 7B, it was confirmed that the cells in the printed support are more likely to survive. That is, considering that the bioink according to an embodiment has biocompatiblility and bio-affinity, the bioink may be used as a variety of biomaterials such as a skin graft, a bone graft, a molded filler, a dental material, a peeling material, a hemostatic material, a support for cell culture, and the like.

According to the one or more embodiments, a hydrogel composition which is composed of natural biocompatible substances is not only non-toxic, but also characterized with high viscosity characteristics, resulting in high mechanical stability or long persistence. Thus, the hydrogel composition may be usefully utilized as a bioink composition for bioprinting, a support in tissue engineering, or a soft tissue filler.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A hydrogel bioink composition for bioprinting, comprising:
   16% by weight to 18% by weight of collagen with respect to the total amount of the hydrogel bioink composition; and
   0% by weight to 4% by weight of hyaluronic acid with respect to the total amount of the hydrogel bioink composition,
   wherein the hydrogel bioink composition does not further comprise a cross-linking agent, and
   wherein the hydrogel bioink composition has an elastic modulus in a range of 6,900 Pa to 9,500 Pa.

2. The hydrogel bioink composition of claim 1, wherein the hydrogel bioink composition further comprises thrombin.

3. The hydrogel bioink composition of claim 1, wherein the hydrogel bioink composition is used for skin regeneration.

4. The hydrogel bioink composition of claim 1, wherein the hydrogel bioink composition is laden with cells.

5. The hydrogel bioink composition of claim 4, wherein the cells are stem cells, sensory cells, brain cells, germ cells, epithelial cells, immune cells, cartilage cells, bone cells, or cancer cells.

6. A method of preparing a biocompatible structure, the method comprising:
   preparing a hydrogel bioink composition according to claim 1; and
   3D-printing the composition to produce a support.

7. The method of claim 6, wherein the method further comprises printing by layering cells on the support.

* * * * *